United States Patent
Fukamizu et al.

(10) Patent No.: US 10,647,956 B2
(45) Date of Patent: May 12, 2020

(54) METHOD FOR ISOLATING, REMOVING AND ANALYZING CELLS

(71) Applicants: UBE INDUSTRIES, LTD., Ube-shi, Yamaguchi (JP); UNIVERSITY OF TSUKUBA, Tsukuba-shi, Ibaraki (JP)

(72) Inventors: Akiyoshi Fukamizu, Tsukuba (JP); Jun-Dal Kim, Tsukuba (JP); Masahiko Hagihara, Ube (JP); Yukinori Wada, Ube (JP)

(73) Assignees: UBE INDUSTRIES, LTD., Yamaguchi (JP); UNIVERSITY OF TSUKUBA, Ibaraki (JP)

( * ) Notice: Subject to any disclaimer, the term of this patent is extended or adjusted under 35 U.S.C. 154(b) by 0 days.

(21) Appl. No.: 15/546,055

(22) PCT Filed: Jan. 26, 2016

(86) PCT No.: PCT/JP2016/052205
§ 371 (c)(1),
(2) Date: Jul. 25, 2017

(87) PCT Pub. No.: WO2016/121766
PCT Pub. Date: Aug. 4, 2016

(65) Prior Publication Data
US 2018/0016542 A1    Jan. 18, 2018

(30) Foreign Application Priority Data
Jan. 26, 2015  (JP) ................................. 2015-012850
Jan. 26, 2015  (JP) ................................. 2015-012851

(51) Int. Cl.
*C12M 1/00*    (2006.01)
*G01N 1/40*    (2006.01)
(Continued)

(52) U.S. Cl.
CPC ............. *C12M 47/02* (2013.01); *C08L 79/08* (2013.01); *C12M 25/02* (2013.01);
(Continued)

(58) Field of Classification Search
CPC ..... C12M 47/02; C12M 25/02; G01N 1/4077; G01N 2001/4088; G01N 33/502; C08L 79/08; C12N 11/08
See application file for complete search history.

(56) References Cited

U.S. PATENT DOCUMENTS 4,228,243 A * 10/1980 Iizuka .................... C12M 23/34
435/294.1
2006/0188392 A1    8/2006 Tanaka et al.
(Continued)

FOREIGN PATENT DOCUMENTS

DE    10 2013 203 050 A1    8/2014
EP          1947170 A1    7/2008
(Continued)

OTHER PUBLICATIONS

Hulkower, K.I. et al. (Mar. 11, 2011). "Cell migration and invasion assays as tools for drug discovery," *Pharmaceutics* 3(1):107-124.
(Continued)

*Primary Examiner* — Sean C. Barron
(74) *Attorney, Agent, or Firm* — Mintz Levin Cohn Ferris Glovsky and Popeo PC

(57) ABSTRACT

The purpose of the present invention is to provide a method for isolating, removing and analyzing cells. Provided is a method for isolating, removing and analyzing cells by filtering a liquid specimen containing cells through a porous polyimide film, and subjecting the cells captured by the film which did not pass through the porous polyimide film, or the cells in the liquid specimen which did pass through the porous polyimide film, to an examination of one or more cell
(Continued)

properties selected from a group consisting of cell number or type, internal or external cell structure, type or amount of cell surface antigen, type or amount of material secreted from cells, cell adhesion, and cell survival rate.

15 Claims, 5 Drawing Sheets

(51) Int. Cl.
   *C12M 1/12* (2006.01)
   *C08L 79/08* (2006.01)
   *C12N 11/08* (2020.01)
   *G01N 33/50* (2006.01)

(52) U.S. Cl.
   CPC ............ *G01N 1/4077* (2013.01); *C12N 11/08* (2013.01); *G01N 33/502* (2013.01); *G01N 2001/4088* (2013.01)

(56) References Cited

U.S. PATENT DOCUMENTS

| | | | |
|---|---|---|---|
| 2010/0266562 A1 | 10/2010 | Humes et al. | |
| 2011/0290112 A1* | 12/2011 | Liu | B01D 53/228 95/54 |
| 2012/0141975 A1 | 6/2012 | Sato et al. | |
| 2012/0207999 A1* | 8/2012 | Ohya | C08J 5/18 428/220 |
| 2013/0045355 A1 | 2/2013 | Ohya et al. | |
| 2013/0323712 A1 | 12/2013 | Sato et al. | |
| 2014/0255636 A1 | 9/2014 | Odeh et al. | |

FOREIGN PATENT DOCUMENTS

| | | | |
|---|---|---|---|
| EP | 2692853 A1 | | 2/2014 |
| JP | 63196286 | * | 8/1988 |
| JP | 2001-324500 A | | 11/2001 |
| JP | 2006-075140 A | | 3/2006 |
| JP | 2014-141490 A | | 8/2014 |
| WO | 2004/083852 A1 | | 9/2004 |
| WO | 2011/00936 A1 | | 1/2011 |
| WO | 2011/043467 A1 | | 4/2011 |
| WO | 2011/125988 A1 | | 10/2011 |
| WO | 2012/070622 A1 | | 5/2012 |

OTHER PUBLICATIONS

Mastyugin, V. et al. (Dec. 2004). "A quantitative high-throughput endothelial cell migration assay," *J Biomol Screen* 9(8):712-718.
International Search Report dated Apr. 19, 2016 corresponding to International Patent Application No. PCT/JP/2016/052205, filed on Jan. 26, 2016; 2 pages.

* cited by examiner

METHOD FOR ISOLATING, REMOVING AND ANALYZING CELLS

TECHNICAL FIELD

The present invention relates to a method for isolating, removing and analyzing cells using a porous polyimide film.

BACKGROUND ART

Although cells are typically present in the body in the form of three-dimensional clusters, in the case of classical plate culturing, cells are cultured in a single layer in a form in which they adhere to a container.

There have been many cases reported in which the properties of cells vary considerably due to differences in the culturing environment. In addition, with respect to suspension culturing in which cells are suspended in a liquid culture medium, although there are cells that are suitable for suspension culturing, there are also cells that are not.

Various types of systems and kits that use these cells have been developed in recent years due to accelerated drug development research and improved evaluation technologies. As exemplified by ELISA kits, which use a color reaction to determine the produced amount of a substance by combining an antigen-antibody reaction and enzyme reaction, and FRET or BRET, which utilize a phenomenon by which energy transfer occurs according to the proximity of two target sites in a form in which it is measured as light, novel methodologies demonstrating high sensitivity, high intensity and high selectivity have been developed through the utilization of numerous principles (NPT 1 and 2).

Among these screening methods, various types of kits and methods have been proposed and implemented based on the principle of cell migration phenomena. Examples of methods that have been developed include a method consisting of fabricating an opening in confluent cultured cells and comparing the phenomenon by which the opening is filled in terms of wound healing rate as described in PTL 1, and a method consisting of punching numerous holes of a fixed size in an insert culture-like structure and comparing the chemotaxis of a compound by cell migration as described in PTL 2. The method described in PTL 2 in particular has already been applied and implemented in various forms. In addition, attempts have also been made in the manner of PTL 3, in which evaluations are carried out by using cell motility per se as the target and monitoring changes in protoplasmic streaming by carefully examining the Brownian movement and protoplasmic streaming of cells, and in the manner of PTL 4, which utilizes inkjet technology to regularly disseminate a large number of cells in narrow regions followed by monitoring and examining the movement thereof.

In the case of using cell motility or migration phenomena for evaluation of new drug development and the like, although this is extremely appealing since it becomes possible to identify interesting properties of cells with respect to quantitative performance and clarity as indicated by prior research, on the other hand, there also many cases requiring extremely complicated systems and intricate apparatuses or cases requiring considerable effort in terms of time and processing, thereby resulting in the desire for the development of easier and faster evaluation methods.

In addition, there are cases in which the status of cells contained in biological samples change corresponding to the status of a portion of or the entire body. For example, treatment methods are known that remove leukocytes that have been activated in associated with some form of disease based on a change in cell status.

Therapy for Removal of Blood Components from Blood Samples

Blood contains numerous types of cells, including leukocytes and erythrocytes. In cellular diseases such as autoimmune diseases, the body's own cells are known to overreact as a result of having become excessively active, and the pharmaceutical-induced suppression of the immune response or removal of cells per se is employed as a medical practice. For example, methodologies are known in which rheumatic diseases, Crohn' disease or ulcerative colitis and the like are treated by removing highly adhesive leukocytes and other cells by packing beads or fibers in the form of a column and allowing blood to pass through the spaces there between (PTL 5, 6 and 7, and NPT 3). In addition, research has been published that verifies efficacy with respect to respiratory diseases as well (NPT 4). Moreover, a method has also been reported that consists of packing beads having antibody immobilized on the surface thereof into the form of a column and selectively acquiring cells that present the same antigen (PTL 8).

Although fibers or beads and the like are used for these carrier bodies, since they structurally consist of an aggregation of straight lines and spherical surfaces, they lack similarity with biological structures, and since they also do not have the property of structurally acquiring cells, they are required to be provided with numerous opportunities and be adsorbed with highly adhesive cells. Since prolonged contact with equipment can be a factor that induces unexpected thrombus formation or blood cell activation, there is a desire for an easier and faster cell removal method that demonstrates a low level of blood activation. Thus, being able to easily and rapidly evaluate the properties of not only blood cells, but also cells present in biological samples, would lead to easy and rapid evaluation of the body's status.

Porous Polyimide Film

The term "polyimide" is a general term for polymers including imide bonds in the repeating unit. An "aromatic polyimide" is a polymer in which aromatic compounds are directly linked by imide bonds. An aromatic polyimide has an aromatic-aromatic conjugated structure via an imide bond, and therefore has a strong rigid molecular structure, and since the imide bonds provide powerful intermolecular force, it has very high levels of thermal, mechanical and chemical properties.

Porous polyimide films have been utilized in the prior art for filters and low permittivity films, and especially for battery-related purposes, such as fuel cell electrolyte membranes and the like. PTLs 9 to 11 describe porous polyimide films with numerous macro-voids, having excellent permeability for gases and the like, high porosity, excellent smoothness on both surfaces, relatively high strength and, despite high porosity, also excellent resistance against compression stress in the film thickness direction. All of these are porous polyimide films formed via amic acid.

PRIOR ART DOCUMENTS

Patent Literature

[PTL 1] Japanese Patent No. 3682772
[PTL 2] Japanese Patent No. 4857292

[PTL 3] Japanese Patent No. 4507060
[PTL 4] Japanese Patent No. 5024823
[PTL 5] Japanese Patent No. 2835923
[PTL 6] Japanese Patent No. 3812909
[PTL 7] Japanese Patent No. 4473324
[PTL 8] Japanese Patent No. 4196592
[PTL 9] WO2010/038873
[PTL 10] Japanese Unexamined Patent Publication No. 2011-219585
[Patent Document 11] Japanese Unexamined Patent Publication No. 2011-219586

Non-Patent Literature

[NPT 1] ORIS™ CELL-BASED ASSAYS brochure
[NPT 2] ASCB 2015 POSTER, An Automatable 3-Dimensional Cell Invasion Assay Compatible with High Content Analysis, Fronczak et. al.
[NPT 3] Hagiwara et al, Journal of Surgical Research 171, 777-782 (2011)
[NPT 4] ONORATI et al. Ann Thorac Surg 2011; 92: 111-21

DISCLOSURE OF THE INVENTION

Problems to be Solved by the Invention

An object of the present invention is to provide a method for isolating, removing and/or analyzing cells, a method for screening for cell activation inhibitors, a device and a kit for using with the method of the present invention, and the use of a polyporous substance in the method of the present invention.

Means for Solving the Problems

As a result of conducting extensive studies to solve the aforementioned problems, the inventors of the present invention found that cells can be isolated, removed and analyzed both easily and rapidly by using a polyimide porous film, thereby leading to the present invention.

The method of the present invention can also be used to screen substances capable of affecting the properties of cells.

The present invention includes the following aspects, although not limited thereto.

Aspect 1

A method for isolating, removing and/or analyzing cells, including: filtering a liquid sample containing cells with a polyimide porous film, and examining one or more cell properties selected from the group consisting of the number or type of cells, external or internal structure of the cells, type or amount of cell surface antigens, type or amount of substances secreted from the cells, cell adhesion and cell survival rate for cells that were captured in the polyimide porous film without being filtered by the film as well as cells in the liquid sample that passed through the polyimide porous film.

Aspect 2

The method described in Aspect 1, wherein the target cells are activated cells.

Aspect 3

The method described in Aspect 2, wherein the activated cells are activated leukocytes.

Aspect 4

The method described in any of Aspects 1 to 3, which includes a step for pretreating all or a portion of the surface of the polyimide porous film prior to the filtration step.

Aspect 5

The method described in Aspect 4, wherein surface treatment of the polyimide porous film is carried out using one or more agents or treatment methods selected from the group consisting of an anticoagulant, collagen, poly-L-lysine, UV light, plasma irradiation and the product of bonding pyridyl disulfide to a terpolymer composed of polyethylene oxide, polypropylene oxide and polyethylene oxide (PDS bound to a hydrophilic resin).

Aspect 6

The method described in any of Aspects 1 to 5, wherein the liquid sample containing cells is filtered with the polyimide porous film after having added a cell activator to the liquid sample and culturing the cells.

Aspect 7

A screening method for cell activation inhibitors, including:
(i) adding a cell activator to a liquid sample containing cells followed by culturing the cells depending on the case,
(ii) adding a test substance to the liquid sample of (i),
(iii) filtering the liquid sample of (ii) with a polyimide porous film and examining one or more cell properties selected from the group consisting of the number or type of cells, external or internal structure of the cells, type or amount of cell surface antigens, type or amount of substances secreted from the cells, cell adhesion and cell survival rate for cells that were captured by the polyimide porous film without being filtered by the film as well as cells in the liquid sample that passed through the polyimide porous film, and
(iv) judging the test substance to be a cell activation inhibitor in the case the ratio and/or number of activated cells captured by the polyimide porous film without passing through the film decreases to a greater degree than in the case of not adding the test substance in step (ii), or in the case the ratio and/or number of activated cells in the liquid sample that passed through the polyimide porous film increases to a greater degree than in the case of not adding the test substance in step (ii).

Aspect 8

The method described in any of Aspects 1 to 7, wherein the liquid sample containing cells contains one or more types of cells selected from the group consisting of primary cultured cells, established cells and isolated blood cells.

Aspect 9

The method described in any of Aspects 1 to 7, wherein the liquid sample containing cells is a biological sample selected from the group consisting of blood, urine, sweat, accumulated coelomic fluid, body cavity washings and sputum.

Aspect 10

The method described in any of Aspects 1 to 9, wherein the filtration is that selected from the group consisting of natural gravity filtration, centrifugal filtration, vacuum filtration and pressure filtration.

Aspect 11

The method described in any of Aspects 1 to 10, including additionally culturing cells present in the liquid sample that passed through the polyimide porous film.

Aspect 12

The method described in any of Aspects 1 to 10, including additionally culturing cells captured in the polyimide porous film without passing through the film while still applied to the polyimide porous film.

Aspect 13

The method described in any of Aspects 1 to 12, wherein the polyimide porous film is a polyimide porous film containing a polyimide obtained from a tetracarboxylic dianhydride and a diamine.

Aspect 14

The method described in Aspect 13, wherein the polyimide porous film is a colored polyimide porous film obtained by forming a polyamic acid solution composition containing a polyamic acid solution, obtained from a tetracarboxylic dianhydride and a diamine, and a colored precursor, followed by heat-treating at 250° C. or higher.

Aspect 15

The method described in Aspect 13 or 14, wherein the polyimide porous film is a multilayer-structured polyimide porous film having two different surface and macrovoid layers.

Aspect 16

The method described in Aspect 15, wherein the film thickness of the polyimide porous film is 75 µm or less.

Aspect 17

The method described in any of Aspects 1 to 16, wherein two or more polyimide porous films are used laminated above and below or side to side.

Aspect 18

A device containing a polyimide porous film for use in the method described in any of Aspects 1 to 17.

Aspect 19

A kit containing a polyimide porous film for use in the method described in any of Aspects 1 to 17.

Aspect 20

A use of a polyimide porous film for the method described in any of Aspects 1 to 17.

Effects of the Invention

The use of a polyimide porous film according to the method of the present invention makes it possible to easily and rapidly isolate, remove and analyze cells. The method of the present invention can also be used to screen substances capable of affecting cell properties.

In addition, the method of the present invention also makes it possible to rapidly and easily determine the body's status by in vitro examination using a sample obtained from the body.

MODE FOR CARRYING OUT THE INVENTION

Figure 1:
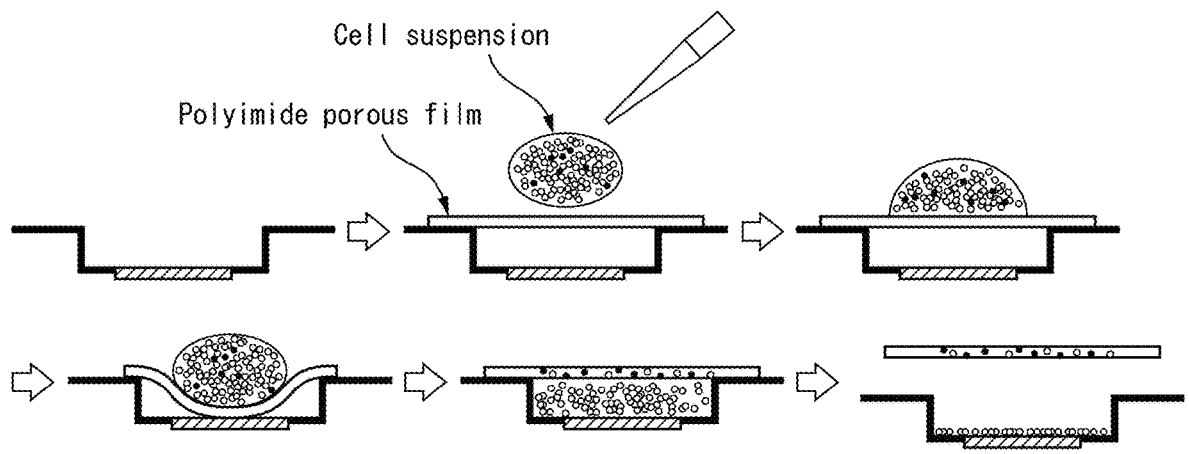
FIG. 1 is a schematic diagram showing one aspect for filtering a liquid sample containing cells (cell suspension) with a polyimide porous film as a typical example of the method of the present invention. (1) (Cell Filtration—Basic System 1)

One aspect of the present invention relates to a method for isolating, removing and/or analyzing cells. The present invention also relates to a screening method for cell activation inhibitors as one aspect of the method for isolating, removing and/or analyzing cells.

The inventors of the present invention found that, when a liquid sample containing cells (cell suspension) or blood sample is passed through a polyimide porous film, the cell permeability of the polyimide porous film is affected by the size and properties of cells placed on the film, thereby leading to the present invention. In the case of filtering adhesive cells, nearly all of the cells were determined to be captured within the polyimide porous film. Moreover, since cells having a small size, and particularly suspended cells, easily pass through the film, it was presumed that it would be possible to be able to reflect the status of those cells in the case of targeting small suspended cells, and when this was verified using established immune system cells activated with phorbol ester, a phenomenon was discovered by which hardly any of the cells that induced inflammation passed through the polyimide porous film. Similarly, the passage rate of the cells is able to be restored by making it possible to inhibit this inflammatory state. Namely, it would be possible to a certain degree to universally evaluate an inflammatory state by evaluating passage through a polyimide porous film that can be carried out in a short period of time. This is the first discovery of a single-film evaluation system suitable for rapid screening.

I. Method for Isolating, Removing and/or Analyzing Cells

One aspect of the present invention relates to a method for isolating, removing and/or analyzing cells. The method of the present invention for isolating, removing and/or analyzing cells typically includes a system and methodology for filtering a cell suspension with a polyimide porous film and analyzing cell status according to whether cells pass through the polyimide porous film or are captured by the polyimide porous film as a result of performing this procedure. The inventors of the present invention discovered a phenomenon by which a multi-faceted porous structure having a polyimide porous film allows cells to remain in the film or pass there through according to the size and properties of the cells, thereby leading to the present invention. The three-dimensional environment of the polyimide porous film imparts cells with a favorable and diverse environment that is able to allow selection of whether cells remain in the film or pass there through corresponding to the circumstances. The use of this principle makes it possible to analyze cell status without requiring a special apparatus. In addition, cell populations can also be analyzed following isolation using various types of existing analytical instruments. This means that the progression and inhibition of cell activation or inflammation can be analyzed by an extremely simple technique based on transmembrane migration. Application of these methods is expected to facilitate deployment to rapid and easy drug development screening kits and the like resulting in considerable industrial value.

The method of the present invention for isolating, removing and/or analyzing cells includes filtering a liquid sample containing cells with a polyimide porous film, and examining one or more cell properties selected from the group consisting of the number or type of cells, external or internal structure of the cells, type or amount of cell surface antigens, type or amount of substances secreted from the cells, cell adhesion and cell survival rate for cells that were captured in the polyimide porous film without being filtered by the film as well as cells in the liquid sample that passed through the polyimide porous film.

The method of the present invention for isolating, removing and/or analyzing cells can be used to successfully remove activated leukocytes from a blood sample in vitro. This method includes methodology that promotes cell removal therapy by removing activated leukocytes captured by the polyimide porous film. The inventors of the present invention found that the non-fibrous type of multi-faceted porous structure of the polyimide porous film reduces the property of activated cells or cells in an inflammatory state of being able to pass through the film, and in the case of having filtered a blood sample of a patient, discovered a phenomenon by which these cells easily remain within the film. Numerous medical devices have been invented and implemented prior to the present invention. However, these devices employ methods in which cells are adsorbed onto a fibrous or spherical carrier according to the adsorptivity of the cells, and since the filter body per se does not have filtration properties, a large contact area is required. In the case of using the polyimide porous film as a cell filtration body, since the material per se has cell filtration properties, the amount of time the cells contact the body can be made to be extremely short, thereby resulting in the potential for reducing the time required for removal therapy. This serves to reduce the burden on patients required to undergo such treatment. Moreover, since the imparting of unnecessary stress to the blood is reduced, the risk of thrombus formation can also be lowered. This is therefore expected to serve as a material for use in revolutionary new forms of cell removal therapy.

1. Cells

The target of the method of the present invention is a liquid sample containing cells. There are no particular limitations on the type of cells, and the method can be used to proliferate any arbitrary cells.

For example, the cells may be selected from the group consisting of animal cells, insect cells, plant cells, yeast cells and bacteria. Animal cells are largely divided into cells from animals belonging to the subphylum Vertebrata, and cells from non-vertebrates (animals other than animals belonging to the subphylum Vertebrata). There are no particular restrictions on the source of the animal cells, for the purpose of the present specification. Preferably, they are cells from an animal belonging to the subphylum Vertebrata. The subphylum Vertebrata includes the superclass Agnatha and the superclass Gnathostomata, the superclass Gnathostomata including the class Mammalia, the class Aves, the class Amphibia and the class Reptilia. Preferably, they are cells from an animal belonging to the class Mammalia, generally known as mammals. Mammals are not particularly restricted but include, preferably, mice, rats, humans, monkeys, pigs, dogs, sheep and goats.

Although not intended to be limiting, preferably, cells which are selected from, for example, Chinese hamster ovary cells (CHO cells), African green monkey kidney epithelial cells (Vero cells), canine renal tubular epithelial cells (MDCK cells) and a established cell line derived from human liver cancer tissue (huGK-14), are used as mammal cells.

There are also no particular restrictions on sources of plant cells, for the purpose of the present specification. Suitable cells are from plants including bryophytes, pteridophytes and spermatophytes.

Plants from which spermatophyte cells are derived include both monocotyledons and dicotyledons. While not restrictive, monocotyledons include Orchidaceae plants, Poaceae plants (rice, corn, barley, wheat, sorghum and the like) and Cyperaceae plants. Dicotyledons include plants belonging to many subclasses including the subclass Chrysanthemum, the subclass Magnoliidae and the subclass Rosidae.

Algae may be considered cell-derived organisms. These include different groups, from the eubacteria Cyanobacteria (blue-green algae), to eukaryotic monocellular organisms (diatoms, yellow-green algae, dinoflagellates and the like) and multicellular marine algae (red algae, brown algae and green algae).

There are no particular limitations on the types of archaebacteria or bacteria for the purpose of the present specification. Archaebacteria are composed of groups comprising methanogenic bacteria, extreme halophilic bacteria, thermophilic acidophilic bacteria, hyperthermophilic bacteria and the like. Bacteria are selected from the group consisting of, for example, lactic acid bacteria, E. coli, Bacillus subtilis and cyanobacteria.

The types of animal cells or plant cells that may be used for the method of the invention are not particularly restricted, but are preferably selected from the group consisting of pluripotent stem cells, tissue stem cells, somatic cells and germ cells.

The term "pluripotent stem cells", for the purpose of the invention, is intended as a comprehensive term for stem cells having the ability to differentiate into cells of a variety of tissues (pluripotent differentiating power). While not restrictive, pluripotent stem cells include embryonic stem cells (ES cells), induced pluripotent stem cells (iPS cells), embryonic germ cells (EG cells) and germ stem cells (GS cells). They are preferably ES cells or iPS cells. Particularly preferred are iPS cells, which are free of ethical problems, for example. The pluripotent stem cells used may be any publicly known ones, and for example, the pluripotent stem cells described in International Patent Publication No. WO2009/123349 (PCT/JP2009/057041) may be used.

The term "tissue stem cells" refers to stem cells that are cell lines capable of differentiation but only to limited specific tissues, though having the ability to differentiate into a variety of cell types (pluripotent differentiating power). For example, hematopoietic stem cells in the bone marrow are the source of blood cells, while neural stem cells differentiate into neurons. Additional types include hepatic stem cells from which the liver is formed and skin stem cells that form skin tissue. Preferably, the tissue stem cells are selected from among mesenchymal stem cells, hepatic stem cells, pancreatic stem cells, neural stem cells, skin stem cells and hematopoietic stem cells.

The term "somatic cells" refers to cells other than germ cells, among the cells composing a multicellular organism. In sexual reproduction these are not passed on to the next generation. Preferably, the somatic cells are selected from among hepatocytes, pancreatic cells, muscle cells, bone cells, osteoblasts, osteoclasts, chondrocytes, adipocytes, skin cells, fibroblasts, pancreatic cells, renal cells and lung cells, or blood cells such as lymphocytes, erythrocytes, leukocytes, monocytes, macrophages or megakaryocytes.

The term "germ cells" refers to cells having the role of passing on genetic information to the succeeding generation in reproduction. These include, for example, gametes for sexual reproduction, i.e. the ova, egg cells, sperm, sperm cells, and spores for asexual reproduction.

The cells may also be selected from the group consisting of sarcoma cells, established cell lines and transformants. The term "sarcoma" refers to cancer occurring in non-epithelial cell-derived connective tissue cells, such as the bone, cartilage, fat, muscle or blood, and includes soft tissue sarcomas, malignant bone tumors and the like. Sarcoma cells are cells derived from sarcoma. The term "established cell line" refers to cultured cells that are maintained in vitro for long periods and reach a stabilized character and can be semi-permanently subcultured. Cell lines derived from various tissues of various species including humans exist, such as PC12 cells (from rat adrenal medulla), CHO cells (from Chinese hamster ovary), HEK293 cells (from human embryonic kidney), HL-60 cells from (human leukocytes) and HeLa cells (from human cervical cancer), Vero cells (from African green monkey kidney epithelial cells), and MDCK cells (from canine renal tubular epithelial cells). The term "transformants" refers to cells with an altered genetic nature by extracellularly introduced nucleic acid (DNA and the like).

Although not intended to be limiting, the "liquid sample containing cells" targeted by the method of the present invention is preferably a biological sample derived from a mammal such as a human, monkey, dog or cat. Accordingly, the "cells" are preferably animal cells or bacteria contained in a biological sample derived from a mammal.

There are cases in which the status of cells contained in a biological sample changes corresponding to the status or all or a portion of the body. An object of the present invention is to determine the status of the body by analyzing a "liquid sample containing cells" derived from the body. For example, in the case a liquid sample derived from the body contains a large number of activated cells, all (systemic) or a portion of the body is judged to have the possibility of being activated, or in other words, suffering from inflammation. In one aspect of the present invention, the target cells are activated cells (such as activated leukocytes).

2. Liquid Sample Containing Cells

The target of the method of the present invention is a liquid sample containing cells. There are no particular limitations on the liquid sample in the present invention provided it has the possibility of containing cells or bacteria. The liquid sample may be a liquid sample derived from the body, or in other words acquired from the body, or an artificially prepared sample. Furthermore, although the "liquid sample" includes a "blood sample" that is presumed to contain activated leukocytes, in the present description, there are cases in which a sample collected for the purpose of removing activated leukocytes from a blood sample is exclusively referred to as a "blood sample" to distinguish the sample from a "liquid sample". In addition, although the term "liquid sample", as far as it includes a blood sample, is suitably referred to as a "liquid sample, etc.", the terms "liquid sample", liquid sample, etc." and "blood sample" are used interchangeably.

A liquid sample containing cells may also be a cell suspension that contains at least one type of cell consisting of primary cultured cells, established cells and isolated blood cells. Methods used to prepare these cells and liquid samples containing cells are known among persons with ordinary skill in the art.

"Primary cultured cells" refer to cells that have been cultured by initially disseminating tissue or cells collected from the body. In general, these cells refer to cells in a cultured state prior to having carried out a subculturing procedure, and in many cases, are present in the form of a mixture of various cells rather than a single type of cell.

Cells obtained by subculturing primary cultured cells are referred to as subcultured cells. A series of cells for which the ability to proliferate has been maintained by subculturing is referred to as "established cells". Various established cells have been established, and as is described in the section entitled "Cells", examples thereof include PC12 cells (derived from rat adrenal medulla), CHO cells (derived from Chinese hamster ovary), HEK293 cells (derived from human embryonic kidney), HL-60 cells (derived from human leukocytes), HeLa cells (derived from human cervical cancer), Vero cells (derived from African green monkey kidney epithelial cells), MDCK cells (derived from canine renal uriniferous tubule epithelial cells) and HepG2 cells (derived from human hepatoma).

"Isolated blood cells" refer to a group of cells contained in blood (blood cells) that can be isolated from the blood. Blood components consist of blood cell components (cellular components, blood cells), platelets, and plasma components consisting of a suspension of blood cell components and platelets. Blood cell components (blood cells) include erythrocytes, leukocytes and platelets.

The inventors of the present invention found that, among these blood components, leukocytes, and particularly leukocytes activated by inflammation and the like, are selectively captured. Leukocytes refer to immunocompetent cells involved in a wide range of the body's defense mechanisms, and are generally referred to as lymphocytes, granulocytes and monocytes. In the case of using a blood sample, those cells in particular that are selectively captured by the polyimide porous film of the present invention are activated granulocytes. Granulocytes are generally referred to as neutrophils, eosinophils and basophils. Although not intended to be limiting, those cells that are selectively captured in particular are activated eosinophils.

The liquid sample containing cells may be a biological sample selected from the group consisting of blood, urine, sweat, accumulated coelomic fluid, body cavity washings and sputum. Blood samples are as previously described. Urine samples and sweat samples contain leukocytes, erythrocytes and cell components such as urinary casts in particular. Cell components in a sample that have been activated in particular are selectively captured by the polyimide porous film as a result of filtering these biological samples with the polyimide porous film.

3. Cell Activator

In the present invention, the liquid sample containing cells may be filtered with a polyimide porous film after having after having added a cell activator to the liquid sample and culturing the cells.

A "cell activator" is the generic term for a substance that activates cells in vitro or in vivo, and there are no particular limitations thereon. An "inflammation-inducing substance" capable of causing inflammation in cells is included in the concept of "cell activator" as referred to in the present description.

The addition of a cell activator to a liquid sample containing cells is capable of causing a change in one or more cell properties selected from the group consisting of the number or type of cells, external or internal structure of the cells, type or amount of cell surface antigens, type or amount of substances secreted from the cells, cell adhesion and cell survival rate in cells contained in the liquid sample. As a result, a change can occur in cells captured by the polyimide porous film without passing there through and/or cells in the liquid sample that have passed through the polyimide porous film.

A "cell activator" can non-exclusively include inflammatory cytokines such as phorbol ester, diacylglycerol, lipopolysaccharide or TNFα.

4. Polyimide Porous Film

One of the characteristics of the present invention is that it includes a step for filtering a liquid sample containing cells with a polyimide porous film.

3. Porous Polyimide Film

Polyimide is a general term for polymers containing imide bonds in the repeating unit, and usually it refers to an aromatic polyimide in which aromatic compounds are directly linked by imide bonds. An aromatic polyimide has an aromatic-aromatic conjugated structure via an imide bond, and therefore has a strong rigid molecular structure, and since imide bonds have powerful intermolecular force, it has very high levels of thermal, mechanical and chemical properties.

The porous polyimide film used for the invention is preferably a porous polyimide film including (as the main component) a polyimide obtained from a tetracarboxylic dianhydride and a diamine, and more preferably it is a porous polyimide film comprising a polyimide obtained from a tetracarboxylic dianhydride and a diamine. The phrase "including as the main component" means that it essentially contains no components other than the polyimide obtained from a tetracarboxylic dianhydride and a diamine, as constituent components of the porous polyimide film, or that it may contain them but they are additional components that do not affect the properties of the polyimide obtained from the tetracarboxylic dianhydride and diamine.

This also includes colored porous polyimide films obtained by forming a polyamic acid solution composition containing a polyamic acid solution obtained from a tetracarboxylic acid component and a diamine component, and a coloring precursor, and then heat treating it at 250° C. or higher.

Polyamic Acid

A polyamic acid is obtained by polymerization of a tetracarboxylic acid component and a diamine component. A polyamic acid is a polyimide precursor that can be cyclized to a polyimide by thermal imidization or chemical imidization.

The polyamic acid used may be any one that does not have an effect on the invention, even if a portion of the amic acid is imidized. Specifically, the polyamic acid may be partially thermally imidized or chemically imidized.

When the polyamic acid is to be thermally imidized, there may be added to the polyamic acid solution, if necessary, an imidization catalyst, an organic phosphorus-containing compound, or fine particles such as inorganic fine particles or organic fine particles. Also, when the polyamic acid is to be chemically imidized, there may be added to the polyamic acid solution, if necessary, a chemical imidization agent, a dehydrating agent, or fine particles such as inorganic fine particles or organic fine particles. Even if such components are added to the polyamic acid solution, they are preferably added under conditions that do not cause precipitation of the coloring precursor.

Coloring Precursor

For the purpose of the invention, a coloring precursor is a precursor that generates a colored substance by partial or total carbonization under heat treatment at 250° C. or higher.

Coloring precursors to be used for the invention are preferably uniformly dissolved or dispersed in a polyamic acid solution or polyimide solution and subjected to thermal decomposition by heat treatment at 250° C. or higher, preferably 260° C. or higher, even more preferably 280° C. or higher and more preferably 300° C. or higher, and preferably heat treatment in the presence of oxygen such as air, at 250° C., preferably 260° C. or higher, even more preferably 280° C. or higher and more preferably 300° C. or higher, for carbonization to produce a colored substance, more preferably producing a black colored substance, with carbon-based coloring precursors being most preferred.

The coloring precursor, when being heated, first appears as a carbonized compound, but compositionally it contains other elements in addition to carbon, and also includes layered structures, aromatic crosslinked structures and tetrahedron carbon-containing disordered structures.

Carbon-based coloring precursors are not particularly restricted, and for example, they include tar or pitch such as petroleum tar, petroleum pitch, coal tar and coal pitch, coke, polymers obtained from acrylonitrile-containing monomers, ferrocene compounds (ferrocene and ferrocene derivatives), and the like. Of these, polymers obtained from acrylonitrile-containing monomers and/or ferrocene compounds are preferred, with polyacrylnitrile being preferred as a polymer obtained from an acrylonitrile-containing monomer.

The tetracarboxylic dianhydride used may be any tetracarboxylic dianhydride, selected as appropriate according to the properties desired. Specific examples of tetracarboxylic dianhydrides include biphenyltetracarboxylic dianhydrides such as pyromellitic dianhydride, 3,3',4,4'-biphenyltetracarboxylic dianhydride (s-BPDA) and 2,3,3',4'-biphenyltetracarboxylic dianhydride (a-BPDA), oxydiphthalic dianhydride, diphenylsulfone-3,4,3',4'-tetracarboxylic dianhydride, bis(3,4-dicarboxyphenyl)sulfide dianhydride, 2,2-bis(3,4-dicarboxyphenyl)-1,1,1,3,3,3-hexafluoropropane dianhydride, 2,3,3',4'-benzophenonetetracarboxylic dianhydride, 3,3',4,4'-benzophenonetetracarboxylic dianhydride, bis(3,4-dicarboxyphenyl)methane dianhydride, 2,2-bis(3,4-dicarboxyphenyl)propane dianhydride, p-phenylenebis(trimellitic acid monoester acid anhydride), p-biphenylenebis(trimellitic acid monoester acid anhydride), m-terphenyl-3,4,3',4'-tetracarboxylic dianhydride, p-terphenyl-3,4,3',4'-tetracarboxylic dianhydride, 1,3-bis(3,4-dicarboxyphenoxy)benzene dianhydride, 1,4-bis(3,4-dicarboxyphenoxy)benzene dianhydride, 1,4-bis(3,4-dicarboxyphenoxy)biphenyl dianhydride, 2,2-bis[(3,4-dicarboxyphenoxy)phenyl]propane dianhydride, 2,3,6,7-naphthalenetetracarboxylic dianhydride, 1,4,5,8-naphthalenetetracarboxylic dianhydride, 4,4'-(2,2-hexafluoroisopropylidene)diphthalic dianhydride, and the like. Also preferably used is an aromatic tetracarboxylic acid such as 2,3,3',4'-diphenylsulfonetetracarboxylic acid. These may be used alone or in appropriate combinations of two or more.

Particularly preferred among these are at least one type of aromatic tetracarboxylic dianhydride selected from the group consisting of biphenyltetracarboxylic dianhydride and pyromellitic dianhydride. As a biphenyltetracarboxylic dianhydride there may be suitably used 3,3',4,4'-biphenyltetracarboxylic dianhydride.

Any desired diamine may be used as a diamine. Specific examples of diamines include the following.

1) Benzenediamines with one benzene nucleus, such as 1,4-diaminobenzene(paraphenylenediamine), 1,3-diaminobenzene, 2,4-diaminotoluene and 2,6-diaminotoluene;

2) diamines with two benzene nuclei, including diaminodiphenyl ethers such as 4,4'-diaminodiphenyl ether and 3,4'-diaminodiphenyl ether, and 4,4'-diaminodiphenylmethane, 3,3'-dimethyl-4,4'-diaminobiphenyl, 2,2'-dimethyl-4,4'-diaminobiphenyl, 2,2'-bis(trifluoromethyl)-4,4'-diaminobiphenyl, 3,3'-dimethyl-4,4'-diaminodiphenylmethane, 3,3'-dicarboxy-4,4'-diaminodiphenylmethane, 3,3',5,5'-tetramethyl-4,4'-diaminodiphenylmethane, bis(4-aminophenyl)sulfide, 4,4'-diaminobenzanilide, 3,3'-dichlorobenzidine, 3,3'-dimethylbenzidine, 2,2'-dimethylbenzidine, 3,3'-dimethoxybenzidine, 2,2'-dimethoxybenzidine, 3,3'-diaminodiphenyl ether, 3,4'-diaminodiphenyl ether, 4,4'-diaminodiphenyl ether, 3,3'-diaminodiphenyl sulfide, 3,4'-diaminodiphenyl sulfide, 4,4'-diaminodiphenyl sulfide, 3,3'-diaminodiphenylsulfone, 3,4'-diaminodiphenylsulfone, 4,4'-diaminodiphenylsulfone, 3,3'-diaminobenzophenone, 3,3'-diamino-4,4'-dichlorobenzophenone, 3,3'-diamino-4,4'-dimethoxybenzophenone, 3,3'-diaminodiphenylmethane, 3,4'-diaminodiphenylmethane, 4,4'-diaminodiphenylmethane, 2,2-bis(3-aminophenyl)propane, 2,2-bis(4-aminophenyl)propane, 2,2-bis(3-aminophenyl)-1,1,1,3,3,3-hexafluoropropane, 2,2-bis(4-aminophenyl)-1,1,1,3,3,3-hexafluoropropane, 3,3'-diaminodiphenyl sulfoxide, 3,4'-diaminodiphenyl sulfoxide and 4,4'-diaminodiphenyl sulfoxide;

3) diamines with three benzene nuclei, including 1,3-bis(3-aminophenyl)benzene, 1,3-bis(4-aminophenyl)benzene, 1,4-bis(3-aminophenyl)benzene, 1,4-bis(4-aminophenyl)benzene, 1,3-bis(4-aminophenoxy)benzene, 1,4-bis(3-aminophenoxy)benzene, 1,4-bis(4-aminophenoxy)benzene, 1,3-bis(3-aminophenoxy)-4-trifluoromethylbenzene, 3,3'-diamino-4-(4-phenyl)phenoxybenzophenone, 3,3'-diamino-4,4'-di(4-phenylphenoxy)benzophenone, 1,3-bis(3-aminophenyl sulfide)benzene, 1,3-bis(4-aminophenyl sulfide)benzene, 1,4-bis(4-aminophenyl sulfide)benzene, 1,3-bis(3-aminophenylsulfone)benzene, 1,3-bis(4-aminophenylsulfone)benzene, 1,4-bis(4-aminophenylsulfone)benzene, 1,3-bis[2-(4-aminophenyl)isopropyl]benzene, 1,4-bis[2-(3-aminophenyl)isopropyl]benzene and 1,4-bis[2-(4-aminophenyl) isopropyl] benzene;

4) diamines with four benzene nuclei, including 3,3'-bis(3-aminophenoxy)biphenyl, 3,3'-bis(4-aminophenoxy)biphenyl, 4,4'-bis(3-aminophenoxy)biphenyl, 4,4'-bis(4-aminophenoxy)biphenyl, bis[3-(3-aminophenoxy)phenyl]ether, bis[3-(4-aminophenoxy)phenyl]ether, bis[4-(3-aminophenoxy)phenyl]ether, bis[4-(4-aminophenoxy)phenyl]ether, bis[3-(3-aminophenoxy)phenyl]ketone, bis[3-(4-aminophenoxy)phenyl]ketone, bis[4-(3-aminophenoxy)phenyl]ketone, bis[4-(4-aminophenoxy)phenyl]ketone, bis[3-(3-aminophenoxy)phenyl] sulfide, bis[3-(4-aminophenoxy)phenyl] sulfide, bis[4-(3-aminophenoxy)phenyl] sulfide, bis[4-(4-aminophenoxy)phenyl] sulfide, bis[3-(3-aminophenoxy)phenyl]sulfone, bis[3-(4-aminophenoxy)phenyl]sulfone, bis[4-(3-aminophenoxy)phenyl]sulfone, bis[4-(4-aminophenoxy)phenyl]sulfone, bis[3-(3-aminophenoxy)phenyl]methane, bis[3-(4-aminophenoxy)phenyl]methane, bis[4-(3-aminophenoxy)phenyl]methane, bis[4-(4-aminophenoxy)phenyl]methane, 2,2-bis[3-(3-aminophenoxy)phenyl]propane, 2,2-bis[3-(4-aminophenoxy)phenyl]propane, 2,2-bis[4-(3-aminophenoxy)phenyl]propane, 2,2-bis[4-(4-aminophenoxy)phenyl]propane, 2,2-bis[3-(3-aminophenoxy)phenyl]-1,1,1,3,3,3-hexafluoropropane, 2,2-bis[3-(4-aminophenoxy)phenyl]-1,1,1,3,3,3-hexafluoropropane, 2,2-bis[4-(3-aminophenoxy)phenyl]-1,1,1,3,3,3-hexafluoropropane and 2,2-bis[4-(4-aminophenoxy)phenyl]-1,1,1,3,3,3-hexafluoropropane.

These may be used alone or in mixtures of two or more. The diamine used may be appropriately selected according to the properties desired.

Preferred among these are aromatic diamine compounds, with 3,3'-diaminodiphenyl ether, 3,4'-diaminodiphenyl ether, 4,4'-diaminodiphenyl ether, paraphenylenediamine, 1,3-bis(3-aminophenyl)benzene, 1,3-bis(4-aminophenyl)benzene, 1,4-bis(3-aminophenyl)benzene, 1,4-bis(4-aminophenyl)benzene, 1,3-bis(4-aminophenoxy)benzene and 1,4-bis(4-aminophenoxy)benzene being preferred for use. Particularly preferred is at least one type of diamine selected from the group consisting of benzenediamines, diaminodiphenyl ethers and bis(aminophenoxy)phenyl.

From the viewpoint of heat resistance and dimensional stability under high temperature, the porous polyimide film is preferably formed from a polyimide obtained by combination of a tetracarboxylic dianhydride and a diamine, having a glass transition temperature of 240° C. or higher, or without a distinct transition point at 300° C. or higher.

From the viewpoint of heat resistance and dimensional stability under high temperature, the porous polyimide film of the invention is preferably a porous polyimide film comprising one of the following aromatic polyimides.

(i) An aromatic polyimide comprising at least one tetracarboxylic acid unit selected from the group consisting of biphenyltetracarboxylic acid units and pyromellitic acid units, and an aromatic diamine unit, (ii) an aromatic polyimide comprising a tetracarboxylic acid unit and at least one type of aromatic diamine unit selected from the group consisting of benzenediamine units, diaminodiphenyl ether units and bis(aminophenoxy)phenyl units, and/or, (iii) an aromatic polyimide comprising at least one type of tetracarboxylic acid unit selected from the group consisting of biphenyltetracarboxylic acid units and pyromellitic acid units, and at least one type of aromatic diamine unit selected from the group consisting of benzenediamine units, diaminodiphenyl ether units and bis(aminophenoxy)phenyl units.

While not restrictive, the porous polyimide film for use in the method of the invention may be a porous polyimide film with a multilayer structure, having at least two surface layers (A-surface and B-surface), and a macro-void layer sandwiched between the two surface layers. Preferably, the porous polyimide film is a porous polyimide film wherein the macro-void layer has a partition bonded to the surface layers (A-surface and B-surface) and a plurality of macro-voids with mean pore sizes of 10 to 500 μm in the planar direction of the film, surrounded by the partition and the surface layers (A-surface and B-surface), wherein the macro-void layer partition and the surface layers (A-surface and B-surface) each have thicknesses of 0.01 to 20 μm, with a plurality of pores with mean pore sizes of 0.01 to 100 μm, the pores being optionally communicating with each other, and also having a partial or total multilayer structure in communication with the macro-voids, where the total film thickness is 5 to 500 μm and the porosity is 40% or greater and less than 95%.

The total film thickness of the porous polyimide film used for the invention is not limited, but may be 20 to 75 μm according to one mode. Differences in the film thickness may be observed as differences in cell growth rate, cell morphology, cell saturation within the plate, and the like.

According to the invention, when the porous polyimide film used has two different surface layers (A-surface and B-surface), and a macro-void layer sandwiched between the two surface layers, the mean pore size of the holes in the A-surface may differ from the mean pore size of the holes in the B-surface. Preferably, the mean pore size of the holes in the A-surface is smaller than the mean pore size of the holes in the B-surface. More preferably, the mean pore size of the holes in the A-surface is smaller than the mean pore size of the holes in the B-surface, with the mean pore size of the holes in the A-surface being 0.01 to 50 μm, 0.01 μm to 40 μm, 0.01 μm to 30 μm, 0.01 μm to 20 μm or 0.01 μm to 15 μm, and the mean pore size of the holes in the B-surface being 20 μm to 100 μm, 30 μm to 100 μm, 40 μm to 100 μm, 50 μm to 100 μm or 60 μm to 100 μm. Most preferably, the A-surface of the porous polyimide film is a mesh structure having small holes with a mean pore size of no greater than 15 μm, such as 0.01 μm to 15 μm, and the B-surface is a large-hole structure with a mean pore size of 20 μm or greater, such as 20 μm to 100 μm.

The total film thickness of the porous polyimide film used for the invention can be measured using a contact thickness gauge.

The mean pore size of the surface of the porous polyimide film can be determined by measuring the pore area of 200 or more open holes from a scanning electron micrograph of the porous film surface, and calculating the mean diameter from the average value for the pore areas according to the following formula (1), assuming the pore shapes to be circular.

[Mathematical Formula 1]

$$\text{Mean pore size} = 2 \times \sqrt{(Sa/\pi)} \tag{1}$$

(wherein Sa represents the average value for the pore areas)

The porosity of the porous polyimide film used for the invention can be determined by measuring the film thickness and mass of the porous film cut out to a prescribed size, and performing calculation from the basis weight according to the following formula (2).

[Mathematical Formula 2]

$$\text{Porosity (\%)} = (1 - w/(s \times d \times D)) \times 100 \tag{2}$$

(wherein S represents the area of the porous film, d represents the total film thickness, w represents the measured mass, and D represents the polyimide density, the polyimide density being defined as 1.34 g/cm³.)

For example, the porous polyimide films described in International Patent Publication No. WO2010/038873, Japanese Unexamined Patent Publication No. 2011-219585 and Japanese Unexamined Patent Publication No. 2011-219586 may also be used in the method of the invention.

The polyimide porous film that is loaded with cells in the present invention is naturally preferably in a state in which it does not contain cells other than the loaded cells, namely has been sterilized. The method of the present invention preferably includes a step for preliminarily sterilizing the polyimide porous film. The polyimide porous film has extremely superior heat resistance, is lightweight, can be selected in various shapes and sizes as desired, and facilitates sterilization treatment. The polyimide porous film can be sterilized by any arbitrary sterilization treatment such as dry heat sterilization, steam sterilization, sterilization with ethanol or other disinfectant, or electromagnetic radiation sterilization including UV light and gamma rays.

In the present invention, a step may be included for pretreating all or a portion of the surface of the polyimide porous film prior to the filtration step. Surface treatment allows the obtaining of effects such as preventing coagulation in the case the liquid sample is blood, increasing the efficiency of isolation, removal and analysis, or imparting hydrophilicity. Surface treatment of the polyimide porous film may be carried out by carrying out chemical treatment using a surface treatment agent such as anticoagulant, collagen, poly-L-lysine, laminin, gelatin, fibronectin, integrin, insulin, serum or PDS bound to a hydrophilic resin. Alternatively, surface treatment may be carried out by carrying out physical treatment such as treatment with UV light or plasma irradiation.

5. Filtration of Liquid Sample, Etc. Containing Cells by Polyimide Porous Film

One characteristic of the present invention is that it includes a step for filtering a liquid sample, etc. containing cells with a polyimide porous film.

There are no particular limitations on the specific step for filtering the cells with the polyimide porous film. The step described in the present description or any arbitrary technique suitable for applying cells to a membranous carrier can be employed.

In the method of the present invention, the polyimide porous film can be used by immobilizing or simply placing in a Petri dish and the like. The polyimide porous film can also be simply immobilized on a Petri dish or on the depression of a laboratory instrument having a depression by wetting a portion of the film. The use of a glass bottom Petri dish as a receptacle leads to improved efficiency since this allows optical evaluation of the depression to proceed efficiently.

The entire polyimide porous film may be moistened with a phosphate buffer or medium and the like in order to improve the filtration rate and shorten analysis time. In addition, a cell suspension can be placed on a dried polyimide porous film followed by storing in an incubator and carrying out filtration over a long period of time. In addition, in the case of carrying out filtration by placing a cell suspension on a dried polyimide porous film in this manner, moving the position of the polyimide porous film, for example, several minutes after having placed the cell suspension thereon leads to a considerable increase in the filtration rate.

Similarly, filtration may be accelerated by applying pressure to the liquid using a method such as centrifugal force or pressure. In the case of using centrifugal force, the liquid filtration rate can be enhanced by attaching a support stand to the centrifuge tube and spinning in a centrifuge.

Although not intending to be limiting, any arbitrary known filtration technique selected from the group consisting of natural gravity filtration, centrifugal filtration, vacuum filtration and pressure filtration can be applied for filtration. The following non-exclusively indicates aspects for filtering a liquid sample containing cells with a polyimide porous film in the method of the present invention.

(1) (Cell Filtration—Basic System 1) (Natural Gravity Filtration) (FIG. 1) The polyimide porous film is placed on a glass bottom Petri dish and a cell suspension is placed thereon. After allowing liquid to pass through, the film and glass bottom Petri dish are separated, and cells remaining on the glass bottom Petri dish and cells captured in the polyimide porous film are observed either still in the form of viable cells or after having immobilized the cells, followed by evaluating the cells. Cells remaining on the glass bottom Petri dish can be observed directly by using, for example, a light microscope such as an inverted microscope.

(2) (Cell Filtration—Basis System 2) (Natural Gravity Filtration) (FIG. 2) The polyimide porous film is placed on a Petri dish and a cell suspension is placed thereon. After allowing liquid to pass through, the film and Petri dish are separated, and cells captured in the liquid in the Petri dish and in the polyimide porous film are observed either still in the form of viable cells or after having immobilized the cells, followed by evaluating the cells.

(3) (Cell Filtration—Centrifugation Type) (Centrifugal Filtration) (FIG. 3) The polyimide porous film is installed in a centrifuge tube having a support stand followed by adding a cell suspension from above. Cell filtration is carried out by allowing the liquid to pass through the film by centrifugation. The recovered liquid is then observed either still in the form of viable cells or after having immobilized the cells followed by evaluating the cells. In addition, cells captured in the polyimide porous film are also observed and evaluated.

Figure 4:
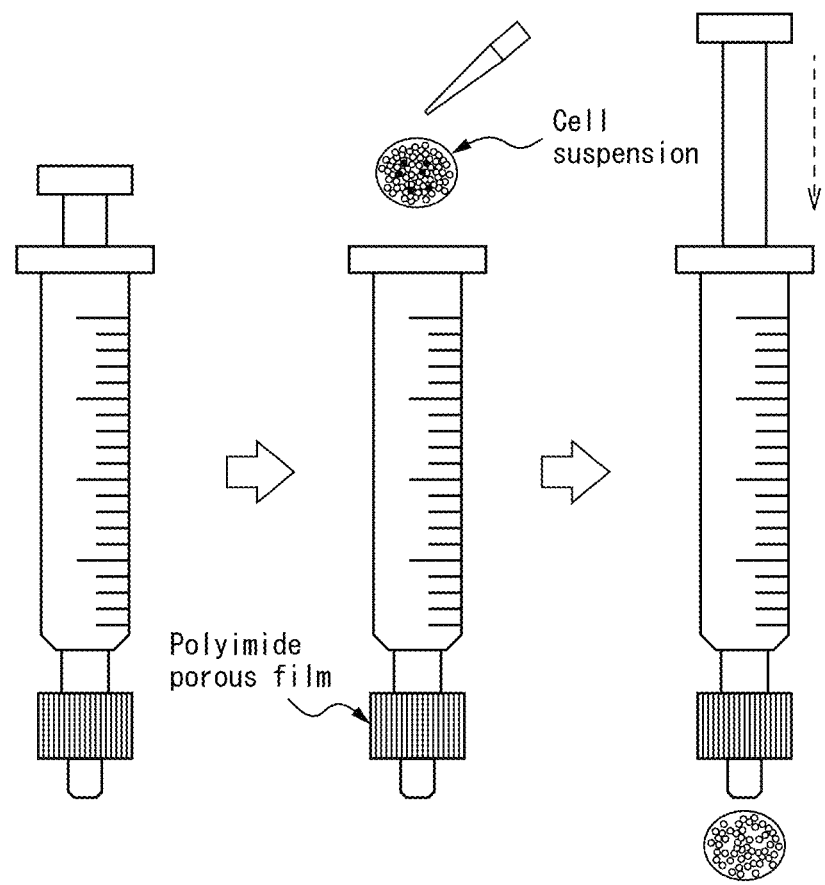
FIG. 4 is a schematic diagram showing one aspect for filtering a liquid sample containing cells (cell suspension) with a polyimide porous film as a typical example of the method of the present invention. (4) (Cell Filtration—Pressure Type)
Figure 5:
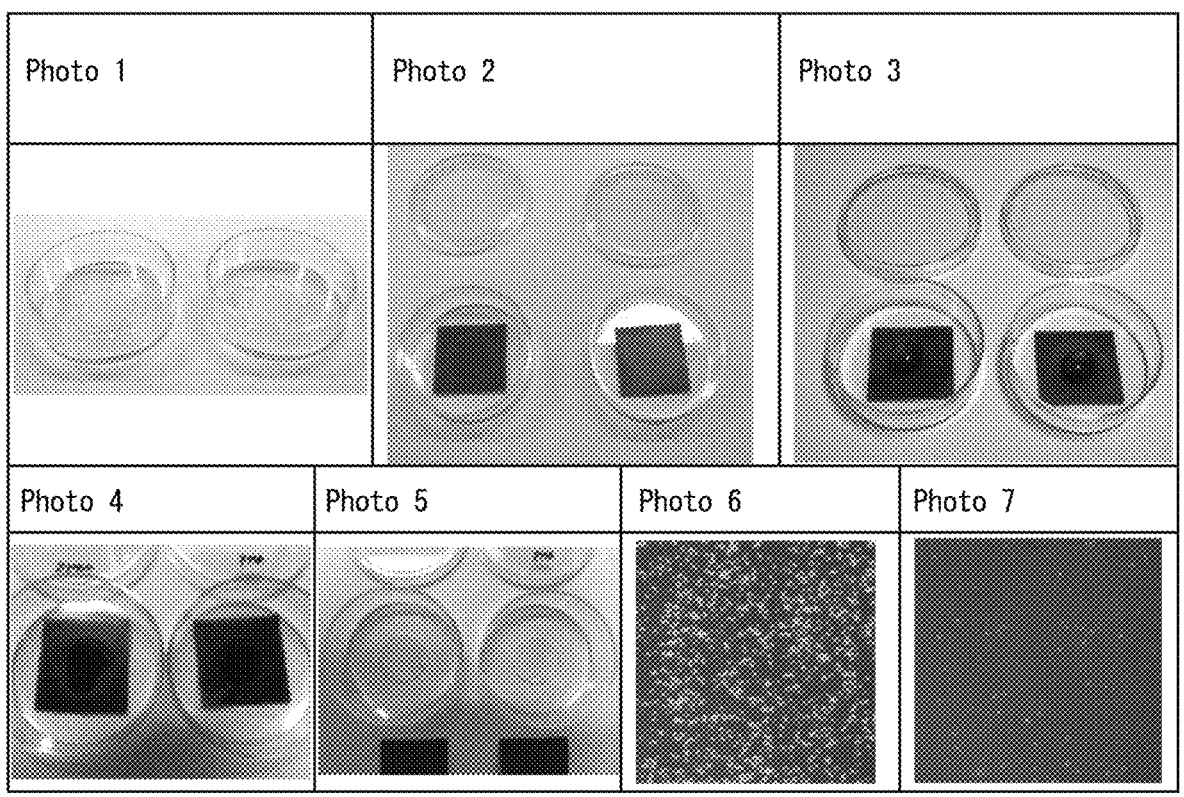
FIG. 5 is a photograph showing the process and results of Example 1.
Figure 6:
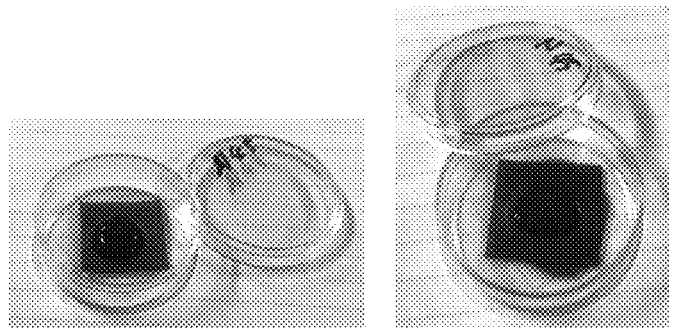
FIG. 6 shows an example of whole blood filtration (Example 2) of the present invention.
Figure 7:
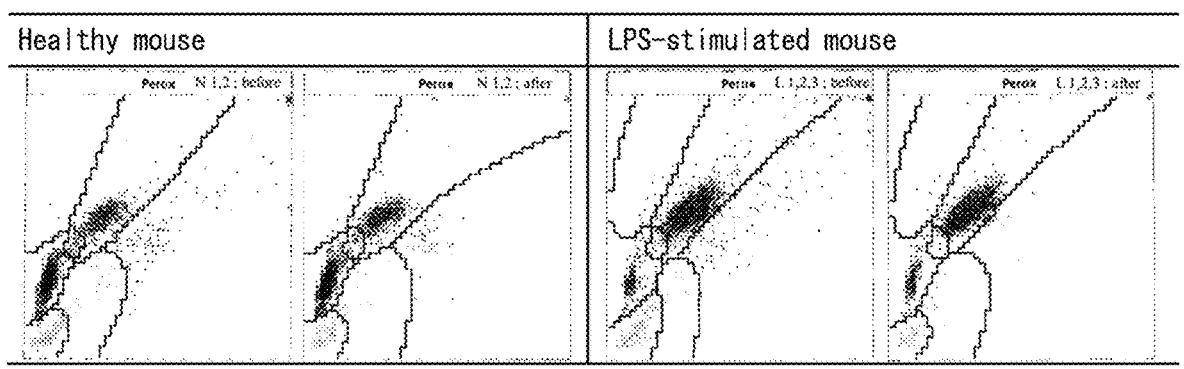
FIG. 7 shows the results of a filtration experiment using mice.

(4) (Cell Filtration—Pressure Type) (Pressure Filtration) (FIG. 4) The polyimide porous film is placed in a filtration device capable of being connected to a syringe followed by charging a cell suspension into the syringe and filtering the suspension with the syringe. Following filtration, the recovered liquid is then observed either still in the form of viable cells or after having immobilized the cells followed by evaluating the cells. In addition, cells captured in the polyimide porous film are also observed and evaluated.

6. Determination of Cell Properties

The method of the present invention includes examining one or more cell properties selected from the group consisting of the number or type of cells, external or internal structure of the cells, type or amount of cell surface antigens, type or amount of substances secreted from the cells, cell adhesion and cell survival rate for cells captured in the polyimide porous film without being filtered by the film as well as cells in the liquid sample that passed through the polyimide porous film, following the filtration step.

The number or type of cells, external or internal structure of the cells, type or amount of cell surface antigens, type or amount of substances secreted from the cells, cell adhesion and cell survival rate can be examined using any known methods for qualitatively or quantitatively analyzing the properties of cells.

The "number or type of cells" can be examined using a device for observing cells such as a flow cytometer or blood cell analyzer. There are cases in which it is sufficient to simply determine an increase or decrease in the number of cells without having to determine the precise number. For example, in the case of having administered a certain cell activation inhibitor to a subject, a change can occur in the ratio of cells captured by the polyimide porous film before and after administration. In the case the ratio of cells captured by the polyimide porous film without passing through the film has decreased, or in the case the ratio of cells in the liquid sample that passed through the polyimide porous film has increased, following administration of a certain substance, this means that the activated cells have decreased, or in other words, that the administered substance acted as a cell activation inhibitor.

An increase or decrease in the number (ratio) of cells can be confirmed using a simple method such as observing with a light microscope or stereoscopic microscope or Giemsa staining by coelomic fluid cytology.

The "external or internal structure of the cells" can be determined using, for example, a microscope such as a light microscope, electron microscope or fluorescence microscope, flow cytometry, western blotting or FIB-SEM.

"Cell surface antigens" is the generic term for various glycoprotein molecules present on the surface of various cells such as human leukocytes. Specific surface antigens are expressed corresponding to the type of cell, such as FCD8α antigen expressed on myeloid dendritic cells and T cells or CD34 antigen or CD133 antigen expressed on hematopoietic stem cells. The type and properties (such as adhesion) of cells can be determined by examining cell surface antigens. Cell surface antigens can be examined by, for example, using specific antibodies to individual cell surface antigens.

Cytokine production or extracellular matrix production and the like may be examined for "substances secreted from the cells". Secretion of IL-6, for example, can be confirmed by a technique such as ELISA.

"Cell adhesion" can be examined using a technique such as a colorimetric method for adhesion to the extracellular matrix.

"Cell survival rate" can be examined using a technique such as trypan blue staining or a LIVE/DEAD® assay.

Either cells that were captured in the polyimide porous film without being filtered by the film or cells in the liquid sample that passed through the polyimide porous film may be examined or both may be examined. Cells in the liquid sample that passed through the polyimide porous film are preferably examined in consideration of the ease and speed of measurement. For example, in the case the number of cells in a liquid sample that have passed through the polyimide porous film has increased, activated cells can be inferred to have decreased, or in other words, inflammation can be inferred to have been alleviated, without having to examine those cells captured by the polyimide porous film without passing there through.

The cell properties of cells captured by the polyimide porous film without passing there through can also be examined as desired by, for example, going through a step such as additionally culturing the cells while still applied to the polyimide porous film.

II. Screening Method for Cell Activation Inhibitors

The present invention includes a screening method for cell activation inhibitors that uses a polyimide porous film. The screening method of the present invention is equivalent to one aspect of the method for isolating, removing and/or analyzing cells of the present invention. The screening method of the present invention includes:

(i) adding a cell activator to a liquid sample containing cells followed by culturing the cells depending on the case, (ii) adding a test substance to the liquid sample of (i), (iii) filtering the liquid sample of (ii) with a polyimide porous film and examining one or more cell properties selected from the group consisting of the number or type of cells, external or internal structure of the cells, type or amount of cell surface antigens, type or amount of substances secreted from the cells, cell adhesion and cell survival rate for cells that were captured by the polyimide porous film without being filtered by the film as well as cells in the liquid sample that passed through the polyimide porous film, and (iv) judging the test substance to have the ability to inhibit cell activation, namely to be a cell activation inhibitor, in the case the ratio and/or number of activated cells captured by the polyimide porous film without passing through the film decreases to a greater degree than in the case of not adding the test substance in step (ii), or in the case the ratio and/or number of activated cells in the liquid sample that passed through the polyimide porous film increases to a greater degree than in the case of not adding the test substance in step (ii).

Steps (i) and (iii) are as described regarding the method used to isolated, remove and analyze cells. The screening method of the present invention is characterized in that, whether or not cells have been activated can be examined by adding a test substance (step (ii)) to cells that have been activated by a cell activator in step (i) and using the degree to which cells are captured by a polyimide porous film as an indicator In the case the ratio and/or number of activated cells captured by the polyimide porous film without passing through the film decreases to a greater degree than in the case of not adding a test substance in step (ii), or the case the ratio and/or number of activated cells in the liquid sample that have passed through the polyimide porous film increases to a greater degree than in the case of not adding the test substance in step (ii), the test substance is judged to be a cell activation inhibitor.

There are no particular limitations on the "test substance", and any arbitrary substance, such as a low molecular weight compound, protein, peptide, glycoprotein or short-chain RNA, can be used as a candidate compound of a cell activation inhibitor.

III. Cell Culturing

The method for isolating, removing and/or analyzing cells of the present invention as well as the screening method of the present invention may further include additionally culturing cells in a liquid sample that have passed through a polyimide porous film. Alternatively, these methods may also include additionally culturing cells captured by the polyimide porous film without passing through the film while still applied to the polyimide porous film. In addition, substances produced by the captured cells may also be analyzed.

Additionally culturing cells that have been isolated by filtering using a polyimide porous film may be used to facilitate analysis of properties of the cells or suitably apply the isolated/cultured cells to the body.

Culturing methods suitable for various cells such as animal cells, plant cells and bacteria are known, and a person with ordinary skill in the art would be able to culture cells on a polyimide porous film using any known method. A cell culture medium can also be suitably prepared corresponding to the type of cells.

Cell culture methods and cell culture media for animal cells may be found in the Cell Culture Media Catalog of Lonza Group, Ltd., for example. Cell culture methods and cell culture media for plant cells may also be found in the Plant Tissue Culturing Media Series by Wako Corp. Japan, for example. Cell culture methods and cell culture media for bacteria may also be found in the General Bacterial Media Catalog of BD Corp., for example.

In the method of the present invention, cells captured by a polyimide porous film can be cultured using any known method after being captured by the polyimide porous film. Culturing of cells using a polyimide porous film can be carried out in the presence of another suspension culture carrier such as a microcarrier or cellulose sponge.

The polyimide porous film may be used after immobilizing in a cell culturing apparatus for culturing the cells while still applied to the polyimide porous film or the cells may be used by suspending in a cell culture medium, and the cells may be placed in a medium or exposed from the medium. Two or more polyimide porous films may be laminated above and below or side to side in a cell culturing apparatus. The laminated aggregate or assembly may be placed in a medium or exposed from the medium.

The cell culturing apparatus able to be used in the method of the present invention may be of any type, and a known cell culturing apparatus can be used provided it contains a polyimide porous film. There are no particular limitations on the form or size of the culturing apparatus, and apparatuses ranging from a Petri dish or test tube to a large-capacity tank can be used suitably. These include, for example, Cell Culture Dish by BD Falcon, and Nunc Cell Factory by Thermo Scientific. By using a porous polyimide film according to the invention, it has become possible to carry out culturing even of cells that have not been capable of natural suspension culture, using an apparatus intended for suspension culture, in a state similar to suspension culturing. The apparatus for suspension culture that is used may be, for example, a spinner flask or rotating culturing flask by Corning, Inc. As an environment allowing a similar function to be obtained, there may be used a hollow fiber culturing system such as the FiberCell® System by Veritas.

The cell culturing apparatus according to the cultured cells of the present invention can be a continuously circulating type or open type so as to allow medium to be continuously added to and recovered from the film on a mesh screen, and culturing can also be carried out with a type of apparatus that exposes the polyimide porous film to air.

IV. Device for Use in the Method of the Present Invention

The present invention further relates to a device containing a polyimide porous film for use in the method of the present invention. In the device of the present invention, two or more polyimide porous films may be laminated above and below or side to side.

The device of the present invention can also suitably contain constituents required to filter samples containing cells in addition to the polyimide porous film. For example, a glass plate or module for supporting the polyimide porous film, a liquid feed tube, a pump, and depending on the case, a sterilized pouch and the like are contained in the device. Although not intended to be limiting, in one aspect thereof, a column or module is contained in which a polyimide porous film is immobilized within a transparent pouch and which is filled with a sterilized liquid. Moreover, the device may also contain constituents for cell culturing, such as a continuous medium supply device, continuous medium circulation device or cell culturing apparatus.

In the method of the present invention, the polyimide porous film can be used in an immobilized state or can be used simply by placing in a sterilized column or module. In addition, use can be initiated in a state in which the polyimide porous film is filled into a column with a sterilized liquid. Cells demonstrating a high level of retention in the film are removed by gravity or by applying pressure from a pump to the column or module while in this state to cause the cells to pass through a single or multiple polyimide porous films installed in the column.

The shape of the column or module can be selected as desired, and examples thereof include a cylindrical shape or disk shape. There are also no particular restrictions with respect to the material composition thereof. A commercially available column can be used, such as the XK Column manufactured by GE Healthcare Inc. or a disposable plastic column manufactured by Thermo Fisher Scientific Inc.

V. Kit

The present invention further relates to a kit containing a polyimide porous film for use in the method of the present invention.

The kit of the present invention can suitably contain constituents required to filter samples containing cells in addition to the polyimide porous film. For example, cells to be applied to the polyimide porous film, a glass plate or module for supporting the polyimide porous film, a liquid feed tube, a pump, and depending on the case, a sterilized pouch and a kit user's manual are contained in the kit. Moreover, the kit may also contain constituents for cell culturing, such as cell culture media, a continuous medium supply device, a continuous medium circulation device or a cell culturing apparatus.

Although not intended to be limiting, one aspect of the present invention includes a package in which a sterilized single or multiple polyimide porous films are stored a transparent pouch that can be used directly for cell culturing, or a film-liquid integrated kit in which a sterile liquid is sealed in the same pouch with the polyimide porous film enabling efficient suction dissemination. In addition, with respect to this film-liquid integrated kit, in an aspect such that blood, from which activated leukocytes have been removed from a blood sample of a subject by the method of the present invention, is returned to the subject, an integrated kit can be provided, for example, that can be used nearby a subject by containing a column or module filled with a sterilized liquid in which the polyimide porous film is immobilized in a sterilized transparent pouch, rupturing the pouch and connecting directly to a pump.

The present invention also relates to the use of the aforementioned method according to the present invention.

EXAMPLES

The present invention will now be explained in greater detail by examples. It is to be understood, however, that the invention is not limited to these examples. A person skilled in the art may easily implement modifications and changes to the invention based on the description in the present specification, and these are also encompassed within the technical scope of the invention. Unless otherwise specified, the term "porous polyimide film" refers to a porous polyimide film with a total film thickness of 25 µm and a porosity of 73%. Each porous polyimide film had at least two different surface layers (A-surface and B-surface), and a macro-void layer sandwiched between the two surface layers. The mean pore size of the holes in the A-surface was 6 µm, and the mean pore size of the holes in the B-surface was 46 µm.

The porous polyimide films used in the following examples were prepared by forming a polyamic acid solution composition including a polyamic acid solution obtained from 3,3',4,4'-biphenyltetracarboxylic dianhydride (s-BPDA) as a tetracarboxylic acid component and 4,4'-diaminodiphenyl ether (ODA) as a diamine component, and polyacrylamide as a coloring precursor, and performing heat treatment at 250° C. or higher.

Example 1

In this example, Jurkat cells which are human leukemia T cell lines were used and activated by adding phorbol esters and culturing the cells, followed by cell filtration using the polyimide porous film. Cell status was analyzed by observing the numbers of filtrated cells.

The Jurkat cells ($1.5 \times 10^6$/ml) are cultured in RPMI1604 medium supplemented with 10% FBS, 10 ng phorbol esters per 1 ml medium is added thereto and then is incubated for 5 min.

Moist areas are made with glycerin around the glass bottom dish previously coated with poly L Lysine (Photo 1), and using the areas, a 2 cm square polyimide porous film sterilized is placed with the B-surface having large holes facing upward (Photo 2). In this state, 100 µl of the previously prepared and activated Jurkat cells are placed as a suspension on the film (Photo 3). When incubated in a $CO_2$ incubator for 12 hours, almost all of the liquid portion passes through the polyimide porous film (Photo 4), and then the past liquid is obtained in the lower part (Photo 5). The liquid part is carefully removed, the remaining cells are washed twice with phosphate buffer, and fixed with formalin. A similar experiment is carried out using the Jurkat cells supplemented with DMSO instead of phorbol esters, and used as a control experiment. Cells attached to the glass surface after completion of the filtration were compared with the control group (Photo 6) and the phorbol ester group (Photo 7), with an inverted microscope. A large amount of cells was observed in the control group, but almost no cells were observed in the phorbol ester group.

Example 2

Figure 2:
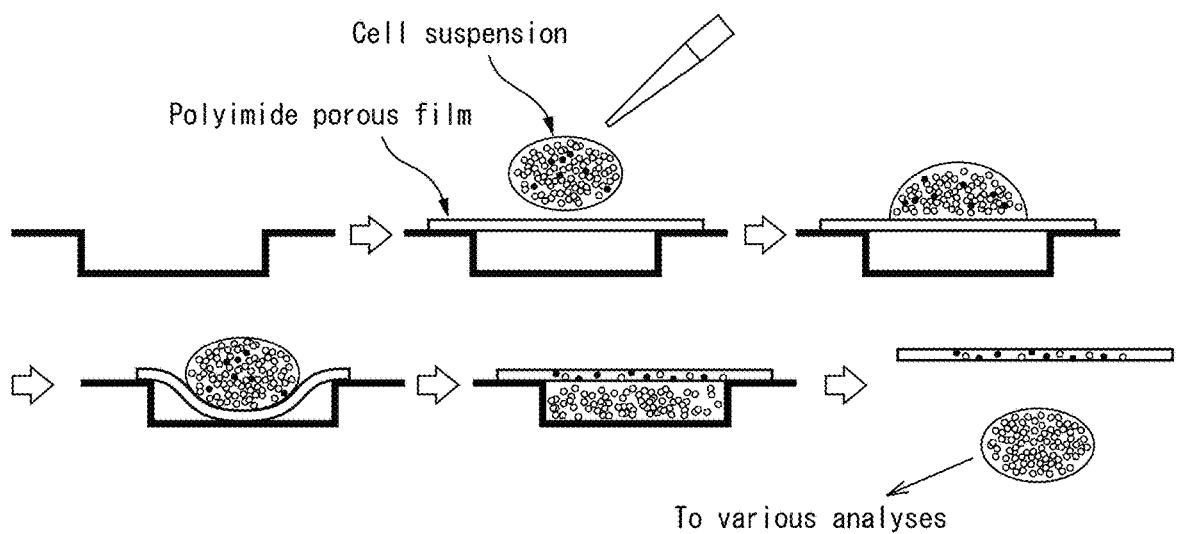
FIG. 2 is a schematic diagram showing one aspect for filtering a liquid sample containing cells (cell suspension) as a typical example of the method of the present invention. (2) (Cell Filtration—Basic System 2)

In this example, lipopolysaccharide was intraperitoneally administered to six 6-week-old Balb/c mice, and 16 hours later, whole blood was collected using a BD Microtina$^R$ MAP microscale blood collection tube. The whole blood was filtered using the polyimide porous films (filtration time: 5 to 10 minutes). The blood cell components before and after the filtration were analyzed by using a blood cell analyzer Advia 2120 provided by SIEMENS Co. As a comparative example, a similar filtration experiment was carried out using five healthy Balb/c mice (FIG. 2).

Figure 3:
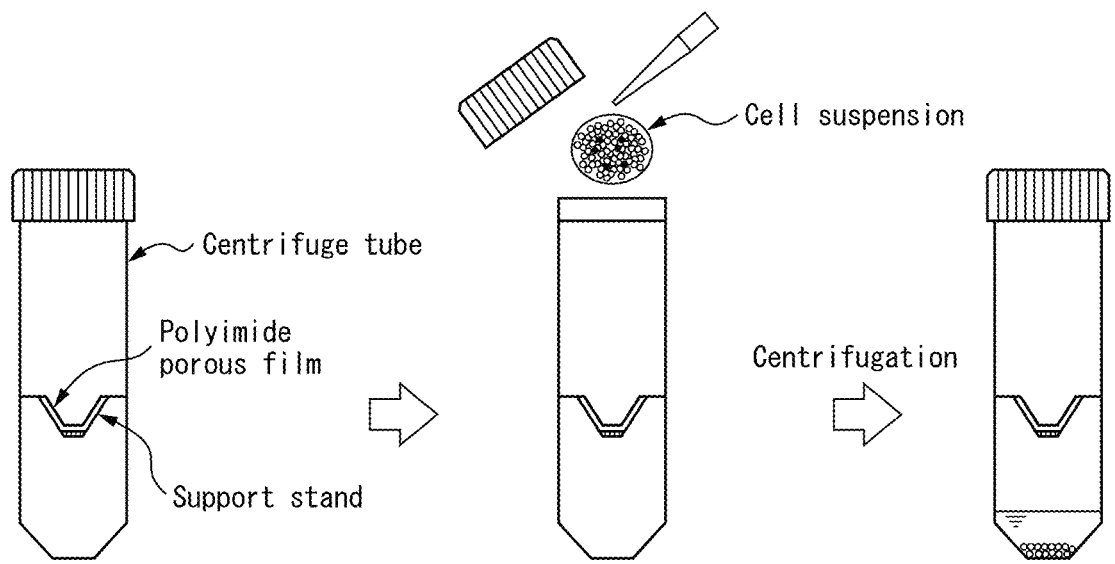
FIG. 3 is a schematic diagram showing one aspect for filtering a liquid sample containing cells (cell suspension) with a polyimide porous film as a typical example of the method of the present invention. (3) (Cell Filtration—Centrifugation Type)

The results are shown in Table 1 and FIG. 3. According to the method of the present invention, a large decrease in white blood cells, particularly eosinophils, was observed. The eosinophil value after filtration was not substantially different between LPS mouse and healthy mouse.

TABLE 1

Comparison of blood cells

| | Cell species | | | | | | | | | |
|---|---|---|---|---|---|---|---|---|---|---|
| | Erythrocyte $10^3/\mu L$ | | Neutrophil $10^3/\mu L$ | | Lymphocyte $10^3/\mu L$ Before/after | | Monocyte $10^3/\mu L$ | | Eosinophil $10^3/\mu L$ | |
| | Before filtration | After filtration | Before filtration | After filtration | Before filtration | After filtration | Before filtration | After filtration | Before filtration | After filtration |
| Healthy | 2.87 | 2.85 | 0.72 | 0.72 | 1.89 | 1.99 | 0.06 | 0.05 | 0.18 | 0.07 |
| LPS | 2.71 | 2.52 | 2.14 | 2.17 | 0.26 | 0.26 | 0.04 | 0.04 | 0.24 | 0.03 |

The invention claimed is:

1. A method for isolating, removing and/or analyzing activated cells, including: filtering a liquid sample containing the cells with a polyimide porous film, and examining one or more cell properties selected from the group consisting of the number or type of cells, external or internal structure of the cells, type or amount of cell surface antigens, type or amount of substances secreted from the cells, cell adhesion and cell survival rate for the cells that were captured in the polyimide porous film without being filtered by the film as well as cells in the liquid sample that passed through the polyimide porous film,
    wherein the polyimide porous film has a three-layer structure consisting of an A-surface layer having a plurality of pores, a B-surface layer having a plurality of pores, and a macro-void layer sandwiched between the two surface layers,
    a mean pore size in the A-surface layer is smaller than a mean pore size in the B-surface layer, and
    the macro-void layer has a partition bonded to the A-surface layer and the B-surface layer, and a plurality of macro-voids surrounded by the partition, the A-surface layer, and the B-surface layer.

2. The method according to claim 1, wherein the activated cells are activated leukocytes.

3. The method according to claim 1, which includes a step for pretreating all or a portion of the surface of the polyimide porous film prior to the filtration step.

4. The method according to claim 3, wherein surface treatment of the polyimide porous film is carried out using one or more agents or treatment methods selected from the group consisting of an anticoagulant, collagen, poly-L-lysine, UV light, plasma irradiation and PDS bound to a hydrophilic resin.

5. The method according to claim 1, wherein the liquid sample containing the cells is filtered with the polyimide porous film after having added a cell activator to the liquid sample and culturing the cells.

6. The method according to claim 1, wherein the liquid sample contains one or more types of cells selected from the group consisting of primary cultured cells, established cells and isolated blood cells.

7. The method according to claim 1, wherein the liquid sample is a biological sample selected from the group consisting of blood, urine, sweat, accumulated coelomic fluid, body cavity washings and sputum.

8. The method according to claim 1, wherein the filtration is selected from the group consisting of natural gravity filtration, centrifugal filtration, vacuum filtration and pressure filtration.

9. The method according to claim 1, further comprising culturing cells present in the liquid sample that passed through the polyimide porous film.

10. The method according to claim 1, further comprising culturing cells captured in the polyimide porous film without passing through the film while still applied to the polyimide porous film.

11. The method according to claim 1, wherein the polyimide porous film comprises a polyimide obtained from a tetracarboxylic dianhydride and a diamine.

12. The method according to claim 11, wherein the polyimide porous film is a colored polyimide porous film obtained by forming a polyamic acid solution composition containing a polyamic acid solution, obtained from a tetracarboxylic dianhydride and a diamine, and a colored precursor, followed by heat-treating at 250° C. or higher.

13. The method according to claim 1, wherein the film thickness of the polyimide porous film is 75 µm or less.

14. The method according to claim 1, wherein two or more polyimide porous films are used laminated above and below or side to side.

15. The method according to claim 1 comprising isolating the cells.

* * * * *